United States Patent [19]

Seltzer et al.

[11] Patent Number: 5,239,103

[45] Date of Patent: Aug. 24, 1993

[54] PROCESS OF MAKING 3,7,9-TRIOXA-1-AZA-2,8-DIPHOSPHAS-PIRO[4,5]DECANES

[75] Inventors: Raymond Seltzer, New City, N.Y.; Paul A. Odorisio, Edgewater, N.J.; Sai P. Shum, Hawthorne, N.Y.; Stephen D. Pastor, Danbury, Conn.

[73] Assignee: Ciba-Geigy Corporation, Ardsley, N.Y.

[21] Appl. No.: 975,043

[22] Filed: Nov. 12, 1992

Related U.S. Application Data

[60] Division of Ser. No. 843,790, Feb. 27, 1992, Pat. No. 5,187,213, which is a division of Ser. No. 702,982, May 20, 1991, Pat. No. 5,132,426, which is a continuation-in-part of Ser. No. 572,728, Aug. 23, 1990, Pat. No. 5,075,482.

[51] Int. Cl.$^5$ ............................................. C07F 9/6584
[52] U.S. Cl. ......................................... 558/77; 558/78; 558/79; 558/119
[58] Field of Search .................... 558/119, 77, 78, 79

[56] References Cited

U.S. PATENT DOCUMENTS

| | | | |
|---|---|---|---|
| 3,553,298 | 1/1971 | Hodan et al. | 558/71 |
| 4,086,304 | 4/1978 | Hutton et al. | 558/71 |
| 4,116,926 | 9/1978 | York | 524/120 |
| 4,402,858 | 9/1983 | Capolupo et al. | 252/400.24 |
| 4,650,894 | 3/1987 | Fisch et al. | 558/71 |
| 4,707,509 | 11/1987 | Fisch et al. | 524/147 |
| 4,751,319 | 6/1988 | Odorisio et al. | 558/16 |
| 4,812,501 | 3/1989 | Odorisio et al. | 524/117 |
| 4,831,178 | 5/1989 | Odorisio | 558/76 |
| 4,888,371 | 12/1989 | Yajima et al. | 521/120 |

FOREIGN PATENT DOCUMENTS 3047443 7/1982 Fed. Rep. of Germany.

*Primary Examiner*—Mary C. Lee
*Assistant Examiner*—Michael G. Ambrose
*Attorney, Agent, or Firm*—Luther A. R. Hall

[57] ABSTRACT

3,7,9-Trioxa-1-aza-2,8-diphosphaspiro[4.5]decanes of formula I

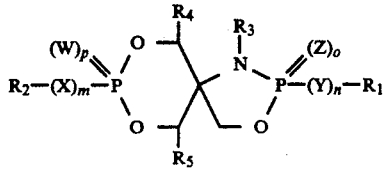

wherein $R_1$ and $R_2$ are independently hydrogen, alkyl, cycloalkyl, bicycloalkyl, tricycloalkyl or aryl; or can be halogen when n or m is zero, $R_3$, $R_4$, $R_5$ and $R_6$ are independently hydrogen, alkyl, aralkyl or aryl;

X and Y are independently —O—, —S— or —$NR_{16}$— where $R_{16}$ is alkyl, cycloalkyl, alkenyl, aryl or aralkyl;

W and Z are independently O or S; and n, m, o and p are independently zero or 1, are effective in stabilizing organic materials against the deleterious effects of oxygen, heat and/or actinic radiation.

2 Claims, No Drawings

PROCESS OF MAKING 3,7,9-TRIOXA-1-AZA-2,8-DIPHOSPHASPIRO[4,5]-DECANES

This is a divisional of Ser. No. 07/843,790, filed on Feb. 27, 1992, now U.S. Pat. No. 5,187,213, issued on Feb. 16, 1993, which is a divisional of Ser. No. 07/702,982, filed on May 20, 1991, now U.S. Pat. No. 5,132,426, issued on Jul. 21, 1992, which is a continuation-in-part of Ser. No. 07/572,728, filed on Aug. 23, 1990, now U.S. Pat. No. 5,075,482, issued on Dec. 24, 1991.

The instant invention pertains to novel substituted 3,7,9-trioxa-1-aza-2,8-diphosphaspiro[4.5]decanes and their use as stabilizers for various organic materials subject to the deleterious effects of oxygen, heat and/or actinic radiation. The instant compounds provide both melt flow stabilization and good resistance against discoloration during polymer processing.

BACKGROUND OF THE INVENTION

U.S. Pat. Nos. 4,751,319; 4,812,501 and 4,831,178 describe aliphatic and aryl esters of 1,3,2-oxazaphospholidines as color improvers and process stabilizers for various polymer substrates.

The instant compounds of this invention are structurally distinguished from the compounds of the prior art, and further provide superior stabilizing performance as well. This is manifested in the superior processing stabilization of polymeric substrates in terms of melt flow stabilization and resistance to discoloration.

OBJECTS OF THE INVENTION

One object of the instant invention is to provide new substituted 3,7,9-trioxa-1-aza-2,8-diphosphaspiro[4.5]-decanes which are effective stabilizers for organic materials subject to oxidative, thermal and/or actinic degradation.

Another object of the invention is to provide stabilized compositions containing an effective stabilizing amount of a 3,7,9-trioxa-1-aza-2,8-diphosphaspiro[4.5]-decane compound of this invention alone or in combination with a hindered phenolic antioxidant and/or a hindered amine thermal stabilizer.

DETAILED DISCLOSURE

The instant invention pertains to substituted 3,7,9-trioxa-1-aza-2,8-diphosphaspiro[4.5]decanes of formula I

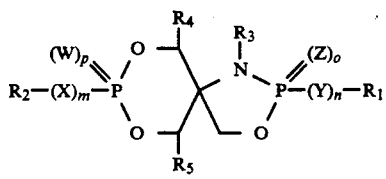

wherein
$R_1$ and $R_2$ are independently hydrogen; a linear or branched alkyl of 1 to 30 carbon atoms; said alkyl optionally terminated with $-OR_7$, $-NR_8R_9$, $-SR_{10}$, $-COOR_{11}$ or $-CONR_{12}R_{13}$, where $R_7$, $R_8$, $R_9$ and $R_{10}$ are independently alkyl of 1 to 20 carbon atoms or alkenyl of 3 to 18 carbon atoms, and $R_{11}$, $R_{12}$ and $R_{13}$ are independently hydrogen or the same meaning as $R_7$; or said alkyl interrupted by one or more $-O-$, $-S-$, $-SO-$, $-SO_2-$, $-CO-$, $-COO-$, $-OCO-$, $-CONR_{14}$, $-NR_{14}CO-$ or $-NR_{15}-$ where $R_{14}$ and $R_{15}$ have the same meaning as $R_{11}$; alkenyl of 3 to 20 carbon atoms; aryl of 6 to 10 carbon atoms; said aryl substituted by one to three substituents selected from the group consisting of alkyl of 1 to 20 carbon atoms, cycloalkyl of 5 to 12 carbon atoms, phenylalkyl of 7 to 15 carbon atoms and the group $-(CH_2)_kCOOR_{20}$ where k is 0, 1 or 2 and $R_{20}$ is hydrogen, alkyl of 1 to 20 carbon atoms or cycloalkyl of 5 to 12 carbon atoms; phenylalkyl of 7 to 9 carbon atoms; bicycloalkyl of 7 to 18 carbon atoms; or tricycloalkyl of 10 to 20 carbon atoms; or $R_1$ and $R_2$ are independently a group of formula II

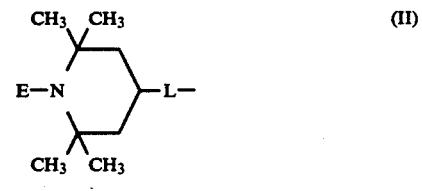

where E is hydrogen, $-OH$, alkyl of 1 to 18 carbon atoms, alkenyl of 3 to 18 carbon atoms, aralkyl of 7 to 15 carbon atoms, alkoxy of 1 to 18 carbon atoms or cycloalkoxy of 5 to 12 carbon atoms; and L is $-O-$ or $-NT-$ where T is hydrogen, alkyl of 1 to 18 carbon atoms or cycloalkyl of 5 to 12 carbon atoms; or when n or m is zero, $R_1$ or $R_2$ is also independently F, Cl, Br or I;

$R_3$ is hydrogen, alkyl of 1 to 20 carbon atoms, phenylalkyl of 7 to 15 carbon atoms or aryl of 6 to 10 carbon atoms;

$R_4$, $R_5$ and $R_6$ are independently hydrogen, alkyl of 1 to 4 carbon atoms or aryl of 6 to 10 carbon atoms;

X and Y are independently $-O-$, $-S-$ or $-NR_{16}-$ where $R_{16}$ is hydrogen, alkyl of 1 to 20 carbon atoms, cycloalkyl of 5 to 12 carbon atoms, alkenyl of 3 to 18 carbon atoms, aryl of 6 to 10 carbon atoms, said aryl substituted by one or two alkyl of 1 to 4 carbon atoms; or phenylalkyl of 7 to 15 carbon atoms;

W and Z are independently O or S; and
n, m, o and p are independently zero or 1.

When p or o is zero, a lone pair of electrons rests on the P atom. When n or m is zero, X or Y is a direct bond.

All of the possible stereoisomers which are predictable, with respect to having multiple asymmetric centers at phosphorous and carbon and a chiral axis, are deemed to be included within the scope of this invention.

Preferably $R_1$ and $R_2$ are the same and are alkyl of 1 to 20 carbon atoms, or when n and m are zero, are also Cl- or Br-, or are
a substituted phenyl of formula III

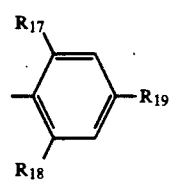

wherein $R_{17}$ and $R_{18}$ are independently hydrogen, alkyl of 1 to 20 carbon atoms, cycloalkyl of 5 to 6 carbon atoms or phenylalkyl of 7 to 9 carbon atoms;

R$_{19}$ is hydrogen, alkyl of 1 to 20 carbon atoms, cycloalkyl of 5 to 6 carbon atoms, phenylalkyl of 7 to 9 carbon atoms or a group —CH$_2$CH$_2$COOR$_{20}$ wherein R$_{20}$ wherein R$_{20}$ is hydrogen or alkyl of 1 to 20 carbon atoms; or where R$_1$ and R$_2$ are cycloalkyl of 5 to 6 carbon atoms; bicycloalkyl of 7 to 10 carbon atoms; or tricycloalkyl of 10 to 12 carbon atoms;

R$_3$ is hydrogen, alkyl of 1 to 20 carbon atoms or phenylalkyl of 7 to 9 carbon atoms;

R$_4$, R$_5$ and R$_6$ are each hydrogen;

X and Y are O or S;

n and m are the same and are zero or 1; and p and o are zero.

Most preferably, R$_1$ and R$_2$ are the same and are alkyl of 4 to 18 carbon atoms or a group of formula III wherein R$_{17}$ and R$_{18}$ are hydrogen or alkyl of 4 to 12 carbon atoms, R$_{19}$ is hydrogen, alkyl of 4 to 12 carbon atoms or is —CH$_2$CH$_2$COOR$_{20}$ where R$_{20}$ is alkyl of 1 to 18 carbon atoms;

R$_3$ is hydrogen, alkyl of 1 to 18 carbon atoms or benzyl;

R$_4$, R$_5$ and R$_6$ are each hydrogen;

X and Y are —O—;

m and n are 1; and o and p are zero.

When any of R$_1$ to R$_{20}$ is alkyl, such alkyl groups are, for example, methyl, ethyl, isopropyl, n-butyl, isobutyl, tert-butyl, tert-amyl, 2-ethylhexyl, n-octyl, tert-octyl, lauryl, n-octadecyl, eicosyl and triacontyl; when said radicals are cycloalkyl, they are, for example, cyclopentyl, cyclohexyl, cyclooctyl and cyclododecyl; when said radicals are alkenyl, they are, for example, allyl, butenyl and oleyl; when said radicals are phenylalkyl, they are, for example, benzyl, phenethyl, α-methylbenzyl and α,α-dimethylbenzyl; when said radicals are aryl, they are, for example, phenyl and naphthyl; when said radicals are alkyl interrupted by —O— or —S—, they are, for example, 3-oxaamyl, 3,6-dioxaoctyl, 3-thiaamyl and 3,6-dithiaoctyl; when said radicals are bicycloalkyl or tricycloalkyl, they are, for example, isobornyl and adamantyl.

The compounds of this invention are prepared by the reaction of the corresponding N-substituted amino-tris(hydroxymethyl)methane and corresponding substituted dichlorophosphine. The starting N-substituted amino-tris(hydroxymethyl)methanes and substituted dichlorophosphines are items of commerce or are readily prepared by known methods. Alternatively, the compounds of this invention are prepared by the reaction of the appropriate nucleophile with the novel 1-substituted-2,8-dihalo-3,7,9-trioxa-1-aza-2,8-diphosphaspiro[4.5]decanes. The novel 1-substituted-2,8-dihalo-3,7,9-trioxa-1-aza-2,8-diphosphaspiro[4.5]decanes are prepared by reaction of a phosphorus trihalide and the appropriate N-substituted amino-tris(hydroxymethyl)methane. These reactions are typically carried out in an inert hydrocarbon or ether solvent, such as toluene or tetrahydrofuran, in the presence of an acid scavenger, such as triethylamine, pyridine or poly(4-vinylpyridine). The instant compounds are preferably prepared by transesterification of the corresponding N-substituted amino-tris(hydroxymethyl)methane and a trialkyl or triaryl phosphite. The transesterifications are preferably carried out in the presence of an alkali metal amide, alkoxide or phenoxide catalyst such as sodium phenoxide, sodium methoxide or lithium amide. Optionally a solvent such as tetraethylene glycol dimethyl ether; 2,4-di-tert-butylphenol; C$_{10}$-C$_{20}$ n-alkanes, isoalkanes, aralkanes or cycloalkanes; decalin; or regular mineral spirits such as Union Chemicals AMSCO Solvent 1005 may be employed.

The instant invention also relates to a facile preferred process for making the compounds of formula I which comprises transesterifying a compound of formula IV

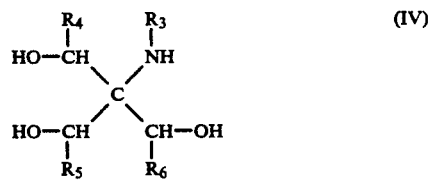

with an essentially stoichiometric amount of a trialkyl or triaryl phosphite of the formula (R$_1$O)$_3$P or (R$_2$O)$_3$P or mixture thereof in the presence of an alkali metal amide, alkoxide or phenoxide catalyst, wherein R$_1$ to R$_6$ are as defined above.

The instant invention also pertains to a stabilized composition which comprises (a) an organic material subject to oxidative, thermal or actinic degradation, and (b) an effective stabilizing amount of a compound of formula I as described above.

The organic material of component (a) is preferably a synthetic polymer; most preferably a polyolefin.

Substrates in which the compounds of this invention are particularly useful are polyolefins such as polypropylene and polyethylene; polystyrene, including especially impact polystyrene; ABS resin; elastomers such as e.g. butadiene rubber, EPM, EPDM, SBR and nitrile rubber.

The instant invention also pertains to stabilized compositions which additionally contain a phenolic antioxidant or a hindered amine compound or a combination thereof. Lists of appropriate phenolic antioxidants and of hindered amine compounds are given below.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber; and lubricating oils.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer, and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxy resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
 1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol.
 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol.
 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol).
 1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
 1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid di-octadecyl ester
3,5-di-tert-butyl-4-hydroxybenzyl-phosphoric acid monoethyl ester, calcium-salt.
 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate.
 1.7. Esters of β-(3,5-di-tert-butyl-4-hydroxyphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide.
 1.8. Esters of β-(5-tert-butyl-4-hydroxy-3-methylphenyl)-propionic acid with monohydric or polyhydric alcohols, for example,
methanol
octadecanol
1,6-hexanediol
neopentyl glycol
thiodiethylene glycol
diethylene glycol triethylene glycol
pentaerythritol
tris-hydroxyethyl isocyanurate
di-hydroxyethyl oxalic acid diamide.

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine.

1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers.

2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethylpiperidin-4-yl)-amino-s-triazin-2-yl]-1,10-diamino-4,7-diazadecane, mixed [2,2,6,6-tetramethylpiperidin-4-yl/$\beta,\beta,\beta',\beta'$-tetramethyl-3,9-(2,4,8,10-tetraoxaspiro[5.5]-undecane)-diethyl] 1,2,3,4-butanetetracarboxylate, mixed [1,2,2,6,6-pentamethylpiperidin-4-yl/$\beta,\beta,\beta',\beta'$-tetramethyl-3,9-(2,4,8,10-tetraoxaspiro[5.5]-undecane)-diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one) and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The stabilizers of the instant invention have good hydrolytic stability. However, co-additives can optionally be employed to improve their hydrolytic stability still further. Examples of such co-stabilizers are:

Nitrogen containing compounds such as those described in U.S. Pat. Nos. 3,553,298 and 4,116,926, the disclosures of which are hereby incorporated by reference;

Long-chain aliphatic amines such as those disclosed in U.S. Pat. Nos. 4,650,894 and 4,707,509, the disclosures of which are hereby incorporated by reference; and Organic acid metal salts such as those described in U.S. Pat. Nos. 4,086,304 and 4,402,858, the disclosure of which are hereby incorporated by reference.

The nitrogen compounds of particular interest are amines which have been shown to improve the hydrolytic stability of pentaerythritol spiro bis phosphites as taught in U.S. Pat. No. 4,888,371 where it is disclosed that an aliphatic, cycloaliphatic or heterocyclic amine as disclosed in U.S. Pat. Nos. 3,553,298 and 4,116,926 can be added to a spiro bis phosphite to improve hydrolytic stability.

Exemplary amines include, for example, trialkanolamines such as triethanolamine, triisopropanolamine and tri-n-propanolamine; dialkanolamines such as diethanol dodecylamine, diethanol octadecylamine, diethanol oleylamine, diethanol octylamine, diethanol hexadecylamine, diisopropanol dodecylamine, diisopropanol octadecylamine and di-n-propanol octadecylamine; dialkanolamines such as diisopropanolamine and diethanolamine; alkane-bis(dialkanolamines) such as ethylene-bis(diethanolamine) and ethylene-bis(diisopropanolamine); heterocyclic amines such as hexamethylenetetramine, piperidine, pyrrolidine, N-methylpiperidine, N-methylpyrrolidine, oxazolidine, morpholine and isooxazolidine; and amine oxides such as lauryldimethylamine oxide and stearyldimethylamine oxide.

The preferred amount of the amine is from 0.01 to 5 parts by weight, preferably from 0.1 to 2 parts by weight, per 100 parts by weight of the spiro bis phosphite.

The following examples are presented for the purpose of illustration only and are not to be construed to limit the nature or scope of the instant invention in any manner whatsoever.

EXAMPLE 1

1-Benzyl-2,8-bis(2,6-di-tert-butyl-4-methylphenoxy)-3,7,9-trioxa-1-aza-2,8-diphosphaspiro[4.5]decane Into a solution of 5 g (24.0 mmol) of N-benzylamino-tris(hydroxymethyl)methane and 13.2 mL (9.6 g, 95.0 mmol) of triethylamine in 140 mL of toluene is added dropwise 15.23 g (47.0 mmol) of 2,6-di-tert-butyl-4-methylphenoxydichlorophosphine at 0° C. After the addition is complete, the reaction mixture is allowed to warm to ambient temperature. After 25 hours, an additional 0.76 g (2.30 mmol) of 2,6-di-tert-butyl-4-methylphenoxydichlorophosphine and 0.66 mL (4.70 mmol) of triethylamine are added to the reaction mixture. One hour after the second addition, the reaction mixture is filtered and the filtrate is concentrated in vacuo to give 20 g of a thick gel. The residue is purified by flash chromatography, using silica gel and a mixture of 97% hexane/2% ethyl acetate/1% triethylamine (by volume) as an eluent, to give 5.9 g (35% yield) of a white solid melting at 81°–85° C.

Analysis: Calcd for $C_{41}H_{59}NO_5P_2$: C, 69.6; H, 8.4; N, 2.0. Found: C, 69.8; H, 8.6; N, 1.7.

EXAMPLE 2

1-Dodecyl-2,8-bis(2,6-di-tert-butyl-4methylphenoxy)-3,7,9-trioxa-1-aza-2,8-diphosphaspiro-[4.5]decane The procedure of Example 1 is repeated using 4.5 g (15.5 mmol) of N-dodecylamino-tris(hydroxymethyl)methane and 8.7 mL (62.2 mmol) of triethylamine in 150 mL of toluene and 10 g (31.1 mmol) of 2,6-di-tert-butyl-4-methylphenoxydichlorophosphine to give 12.8 g of a yellow oil. The residue is purified by flash chromatography, using silica gel and a mixture of 97.5% hexane/1.5% ethyl acetate/1% triethylamine (by volume) as a solvent system, to give 10.1 g (83% yield) of a white solid melting at 45°–50° C.

Analysis: Calcd for $C_{46}H_{77}NO_5P_2$: C, 70.3; H, 9.9; N, 1.8. Found: C, 70.5; H, 10.3; N, 1.6.

EXAMPLE 3

1-(H)-2,8-Bis(2,6-di-tert-butyl-4-methylphenoxy)-3,7,9-trioxa-1-aza-2,8-diphosphaspiro[4.5]decane The procedure of Example 1 is repeated using 1.74 g (14.4 mmol) of tris(hydroxymethyl)aminomethane, 8.07 mL (5.86 g, 58.0 mmol) of triethylamine, 9.31 g (28.9 mmol) of 2,6-di-tert-butyl-4-methylphenoxydichlorophosphine to give 10.5 g of a crude oil. The residue is purified by trituration with hexane to give 3.32 g (37% yield) of an off-white solid melting at 192°–196° C.

Analysis: Calcd for $C_{34}H_{53}NO_5P_2$: C, 66.1; H, 8.7; N, 2.3. Found: C, 66.1; H, 8.8; N, 2.1.

EXAMPLE 4

1-Benzyl-2,8-bis[2,6-di-tert-butyl-4-(2-methoxycarbonylethyl)-phenoxy]-3,7,9-trioxa-1-aza-2,8-diphosphaspiro[4.5]decane The procedure of Example 1 is repeated using 5.48 g (26 mmol) of N-benzylamino-tris(hydroxymethyl)methane, 19.6 g (27 mL, 194 mmol) of triethylamine, 20.44 g (52 mmol) of 2,6-di-tert-butyl-4-(methylpropion-3-yl)phenoxydichlorophosphine and 125 mL of toluene to give 26.8 g of a crude oil. The residue is purified by flash chromatography (silica gel, 90% hexane/9% ethyl acetate/1% triethylamine) to give 13.58 g (62% yield) of a white solid melting at 59°–64° C.

Analysis: Calcd for $C_{47}H_{67}NO_9P_2$: C, 66.3; H, 7.9; N, 1.6. Found: C, 66.1; H, 8.0; N, 1.6.

EXAMPLE 5

1-(H)-2,8-Bis(2,4-di-tert-butylphenoxy)-3,7,9-trioxa-1-aza-2,8-diphosphaspiro[4.5]decane The procedure of Example 1 is repeated using 6.37 g (53 mmol) of tris(hydroxymethyl)aminomethane, 32.23 mL (231 mmol) of triethylamine in 200 mL of toluene and 32.28 g (105 mmol) of 2,4-di-tert-butylphenoxydichlorophosphine in 100 mL of toluene to give 35 g of a crude oil. The residue is purified by trituration with hexane to gave 8.69 g (28% yield) of a white solid melting at 154°–159° C.

Analysis: Calcd for $C_{32}H_{49}NO_5P_2$: C, 65.2; H, 8.4; N, 2.4. Found: C, 65.2; H, 8.4; N, 2.3.

EXAMPLE 6

1-Benzyl-2,8-bis(2,4-di-tert-butylphenoxy)-3,7,9-trioxa-1-aza-2,8-diphosphaspiro[4.5]decane The procedure of Example 1 is repeated using 3.76 g (17.8 mmol) of N-benzylamino-tris(hydroxymethane, 10.92 mL (78.0 mmol) of triethylamine in 150 mL of toluene and 10.93 g (35.6 mmol) of 2,4-di-tert-butylphenoxydichlorophosphine in 50 mL of toluene to give 24.18 g of a crude oil. Upon purification (silica gel, 96.5% hexane/2% ethyl acetate/1.5% triethylamine), 6.75 g (56% yield) of a white solid melting at 62°–70° C. is obtained.

Analysis: Calcd for $C_{39}H_{55}NO_5P_2$: C, 68.9; H, 8.2; N, 2.1. Found: C, 69.1; H, 8.5; N, 2.1.

EXAMPLE 7

1-(H)-2,8-Bis[2,6-di-tert-butyl-4-(2-n-octadecyloxycarbonyl-ethyl)phenoxy]-3,7,9-trioxa-1-aza-2,8-diphosphaspiro[4.5]decane The procedure of Example 1 is repeated using 6.06 g (50 mmol) of tris(hydroxymethyl)aminomethane, 30.6 mL (220 mmol) of triethylamine in 300 mL of toluene and 63.2 g (100 mmol) of 2,6-di-tert-butyl-4-(2-n-octadecyloxycarbonylethyl)phenoxydichlorophosphine in 200 mL of toluene. Upon purification (silica gel, 94% hexane/5% ethyl acetate/1% triethylamine) of 50 g of the crude oil, 21.47 g (34% yield) of a white solid melting at 95°–98° C. is obtained.

Analysis: Calcd for $C_{74}H_{129}NO_9P_2$: C, 71.8; H, 10.5; N, 1.1. Found: C, 71.7; H, 10.6; N, 1.1.

EXAMPLE 8

1-Isobutyl-2,8-dichloro-3,7,9-trioxa-1-aza-2,8-diphosphaspiro[4.5]decane

Into a solution of 23.24 g (14.8 ml, 169 mmol) of phosphorus trichloride in 420 mL of tetrahydrofuran (THF) is added dropwise a solution of 15 g (84.6 mmol) of N-isobutylaminotris(hydroxymethyl)methane and 26.77 g (27.44 mL, 338.4 mmol) of pyridine in 84 mL of THF at −65° C. to −50° C. over a one-hour period of time. After the addition is complete, the reaction mixture is allowed to warm to ambient temperature. After 24 hours of stirring at ambient temperature, the reaction mixture is filtered and the filtrate is concentrated to an oil. The crude oil is purified by distillation to give 17.55 g (68% yield) of a white solid: b.p. 110° C. at 0.01 mmHg.

EXAMPLE 9

1-(H)-2,8-Dichloro-3,7,9-trioxa-1-aza-2,8-diphosphaspiro[4.5]decane

The procedure of Example 8 is repeated using 17.4 mL (200 mmol) of phosphorus trichloride, 12.1 g (100 mmol) of tris(hydroxymethyl)aminomethane and 32.4 mL (400 mmol) of pyridine in 500 mL of acetonitrile to give 16.2 g (65% yield) of a clear oil: $^{31}$P NMR (C$_6$D$_6$): 175,143 ppm.

EXAMPLE 10

1-Isobutyl-2,8-di(1-adamantyloxy)-3,7,9-trioxa-1-azadiphosphaspiro[4.5]decane

Into a solution of 7.53 g (24.6 mmol) of 1-isobutyl-2,8-dichloro-3,7,9-trioxa-1-aza-2,8-diphosphaspiro[4.5]decane (compound of Example 8) in 120 mL of toluene is added dropwise a solution of 7.49 g (49.2mmol) of 1-adamantanol and 5.47 g (7.5 mL, 54.1 mmol) of triethylamine in 70 mL of toluene at −60° to −50° C. over a 45-minute period. After the addition is complete, the reaction mixture is allowed to warm to ambient temperature. After two hours, the reaction mixture is filtered and the filtrate is concentrated in vacuo to give 13.85 g of a crude oil. The residue is purified by flash chromatography (basic alumina, 97% hexane/3% ethyl acetate) to give 7.87 g (60% yield) of a white solid melting at 97°–100° C.

Analysis: Calcd for C$_{28}$H$_{45}$NO$_5$P$_2$: C, 62.6; H, 8.4; N, 2.6. Found: C, 62.6; H, 8.8; N, 2.3.

EXAMPLE 11

1-Isobutyl-2,8-di(n-octadecyloxy)-3,7,9-trioxa-1-aza-2,8-diphosphaspiro[4.5]decane The procedure of Example 10 is repeated using 10.89 g (36 mmol) of 1-isobutyl-2,8-dichloro-3,7,9-trioxa-1aza-2,8-diphosphaspiro[4.5]decane (compound of Example 8) in 200 mL of toluene and 19.25 g (77 mmol) of n-octadecanol and 7.92 g (10.9 mL, 78 mmol) of triethylamine in 100 mL of toluene to give 26.34 g of white solid. The residue is purified by flash chromatography (basic alumina, 3% ethyl acetate/97% hexane) to give 9.23 g (34% yield) of a white solid melting at 33°–39° C. The product is identified by mass spectroscopy: m/z=773.

EXAMPLE 12

1-Isobutyl-2,8-bis(2,4-di-tert-butylphenoxy)-3,7,9-trioxa-1-aza-2,8-diphosphaspiro[4.5]decane The procedure of Example 10 is repeated using 3.65 g 12 mmol) of 1-isobutyl-2,8-dichloro-3,7,9-trioxa-1-aza-2,8-diphosphaspiro[4.5]decane (compound of Example 8), 4.92 g (24 mmol) of 2,4-di-tert-butylphenol and 3.35 mL of triethylamine in 40 mL of THF to give 8 g of an amber oil. The residue is purified by flash chromatography (silica gel, 97% hexane/2% ethyl acetate/1% triethylamine) to give 2.86 g (37% yield) of a white solid melting at 66°–69° C.

Analysis: Calcd for C$_{36}$H$_{57}$NO$_5$P$_2$: C, 67.0; H, 8.9; N, 2.2. Found: C, 67.3; H, 9.3; N, 2.3.

EXAMPLE 13

1-(H)-2,8-Di(4-tert-octylphenoxy)-3,7,9-trioxa-1-aza-2,8-diphosphaspiro[4.5]decane The procedure of Example 10 is repeated using 15 g (60mmol) of 1-(H)-2,8-dichloro-3,7,9-trioxa-1-aza-2,8-diphoshpaspiro[4,5]decane (compound of Example 9), 24.76 g (120 mmol) of 4-tert-octylphenol and 16.7 mL (120 mmol) of triethylamine in 200 mL of THF to give 40 g of a viscous oil. The residue is purified by crystallization from a mixture of 40 mL of ethanol and 2 mL triethylamine to give 1.7 g (5% yield) of a white solid melting at 102°–105° C.

Analysis: Calcd for C$_{32}$H$_{49}$NO$_5$P$_2$: C, 65.2; H, 8.4; N, 2.4. Found: C, 65.1; H, 8.4; N, 2.6.

EXAMPLE 14

1-Benzyl-2,8-diphenyl-3,7,9-trioxa-1-aza-2,8-diphosphaspiro[4.5]decane

The procedure of Example 1 is repeated using 8.85 g (42 mmol) of N-benzylamino-tris-(hydroxymethyl)methane, 11.4 mL (84 mmol) of dichlorophenylphospine and 26 mL (184 mmol) of triethylamine in 200 mL of toluene to give 18 g of a viscous oil. The product is identified by mass spectroscopy: m/z=423.

EXAMPLE 15

1-Isobutyl-2,8-di(n-octadecylthio)-3,7,9-trioxa-1-aza-2,8-diphosphaspiro[4.5]decane The procedure of Example 10 is repeated using 8.72 g (28.5 mmol) of 1-isobutyl-2,8-dichloro-3,7,9-trioxa-1-aza-2,8-diphosphaspiro[4.5]decane, 16.33 g (57 mmol) of n-octadecyl mercaptan and 8.74 mL (63 mmol) of triethylamine in 200 mL of toluene. A white solid (7.11 g) is isolated. The product is identified by mass spectroscopy: m/z=805.

EXAMPLE 16

1-Isobutyl-2,8-bis(dicyclohexylamino)-3,7,9-trioxa-1-aza-2,8-diphosphaspiro[4.5]decane The procedure of Example 10 is repeated using 1-isobutyl-2,8-dichloro-3,7,9-trioxa-1-aza-2,8-diphosphaspiro[4.5]decane, dicyclohexylamine and triethylamine in toluene to afford the desired product.

EXAMPLE 17

1-Isobutyl-2,8-di{2-tert-butyl-4-[2-(isooctyloxycarbonyl)ethyl]-phenoxy}-3,7,9-trioxa-1-aza-2,8-diphosphaspiro[4.5]decane The general procedure of Example 10 is repeated using 3.0 g (9.8 mmol) of 1-isobutyl-2,8-dichloro-3,7,9-trioxa-1-aza-2,8-diphosphaspiro[4.5]decane, 6.6 g (19.8 mmol) of 2-tert-butyl-4-[2-(isooctyloxycarbonyl)ethyl]-phenol and 2.8 mL (19.8 mmol) of triethylamine in 50 mL of toluene at ambient temperature to give 9.3 g of a colorless oil. The residue is purified by flash chromatography (silica gel; 90.2% hexane: 8.3% ethyl acetate: 1.5% triethylamine) to give the title compound in a yield of 8.1 g (90%) as a colorless oil.

Analysis: Calcd for $C_{50}H_{81}NO_9P_2$: C, 66.6; H, 9.1; N, 1.6. Found: C, 67.0; H, 9.5; N, 1.6.

EXAMPLE 18

1-Benzyl-2,8-diphenoxy-3,7,9-trioxa-1-aza-2,8-diphosphaspiro[4.5]decane

A mixture of 5.0 g (23.7 mmol) of N-benzylamino-tris(hydroxymethyl)methane, 12.5 mL (47.4 mmol) of triphenyl phosphite and 0.09 g (0.71 mmol) of sodium phenolate is heated to 110°–118° C. at 9–10 mm Hg removing phenol as it forms. The title compound is formed in a yield of 10.7 g as a white solid and is identified by mass spectrometry: m/z=455.

EXAMPLE 19

1-Isobutyl-2,8-diphenyl-3,7,9-trioxa-1-aza-2,8-diphosphaspiro[4.5]decane

Into a solution of 10.0 g (32.7 mmol) of 1-isobutyl-2,8-dichloro-3,7,9-trioxa-1-aza-2,8-diphosphaspiro[4.5]decane, the compound of Example 8, in 60 mL of tetrahydrofuran (THF) is added dropwise 32.7 mL (65.4 mmol) of a 2M solution of phenyl magnesium chloride in THF at ambient temperature. The title compound is isolated in a yield of 11 g as an oil and identified by mass spectrometry: m/z=389.

EXAMPLE 20

1-Isobutyl-2,8-bis[di(2-ethylhexyl)amino]-3,7,9-trioxa-1-aza-2,8-diphosphaspiro[4.5]decane The procedure of Example 10 is repeated using 5.0 g (16.4 mmol) of 1-isobutyl-2,8-dichloro-3,7,9-trioxa-1-aza-2,8-diphosphaspiro[4.5]decane, the compound of Example 8, 7.9 g (32.8 mmol) of di-2-ethylhexylamine and 4.6 mL (32.8 mmol) of triethylamine in 120 mL of toluene. The title compound is isolated in a yield of 10.2 g as an oil and is identified by mass spectrometry: m/z=715.

EXAMPLE 21

1-Isobutyl-2,8-di(1-methoxy-2,2,6,6-tetramethylpiperidin-4-yloxy)-3,7,9-trioxa-1-aza-2,8-diphosphaspiro[4.5]-decane The procedure of Example 10 is repeated using 4.4 g (14.4 mmol) of 1-isobutyl-2,8-dichloro-3,7,9-trioxa-2,8-diphosphaspiro[4.5]decane, compound of Example 8, 5.4 g (28.8 mmol) of 1-methoxy-2,2,6,6-tetramethyl-4-hydroxypiperidine and 4 mL (28.8 mmol) of triethylamine in 250 mL of toluene to give 10.3 g of a crude oil. The residue is purified by flash chromatography (silica gel; 6% ethyl acetate:2% triethylamine:92% hexane) to give 3.0 g (34% yield) of the title compound.

Analysis: Calcd for $C_{28}H_{55}N_3O_7P_2$: C, 55.3; H, 9.1; N, 6.9. Found: C, 55.1; H, 9.5; N, 6.7.

EXAMPLE 22

1-Ethyl-2,8-di(2,4-di-tert-butylphenoxy)-3,7,9-trioxa-1-aza-2,8-diphosphaspiro[4.5]decane The procedure of Example 1 is repeated using 8.0 g (54 mmol) of N-ethylamino-tris(hydroxymethyl)methane, 30 mL (2.6 mmol) of triethylamine and 33.2 g (108 mmol) of 2,4-di-tert-butylphenoxydichlorophosphine in 320 mL of toluene to give 34.4 g of a crude oil. The residue is purified by flash chromatography (silica gel; 1.5% ethyl acetate: 1.5% triethylamine:978% hexane) to give 8.7 g of the title compound as an off-white solid.

Analysis: Calcd for $C_{34}H_{53}NO_5P_2$: C, 66.1; H, 8.7; N, 2.3. Found: C, 66.2; H, 8.8; N, 2.1.

EXAMPLE 23

1-Benzyl-2,8-di(2,4-di-tert-butylphenoxy)-3,7,9-trioxa-1-aza-2,8-diphosphaspiro[4.5]decane The general procedure of Example 18 is repeated using 1.5 g (7.1 mmol) of N-benzylamino-tris(hydroxymethyl)methane, 9.2 g (14.2 mmol) of tris(2,4-di-tert-butylphenyl) phosphite and 0.04 g (0.71 mmol) of sodium methoxide. The title compound is isolated by crystallization from isopropanol as a white solid and is identified by $^{31}P$ NMR.

$^{31}P$ NMR (200 MHz)(Benzene-$d_6$)(ppm): 142.5; 112.2.

The product is accompanied by variable amounts of 4-benzylamino-2,6,7-trioxa-1-phosphabicyclo[2.2.2]octane identified by $^{31}P$ NMR (200 MHz)(Benzene-$d_6$)(ppm):91.08; and by mass spectrometry: m/z=239.

EXAMPLE 24

1-Benzyl-2,8-di(2,4-di-tert-butylphenoxy)-3,7,9-trioxa-1-aza-2,8-diphosphaspiro[4.5]decane The product of Example 18 is reacted with two equivalents of 2,4-di-tert-butylphenol and sodium methoxide at reduced pressure and at an elevated temperature to afford the title compound.

EXAMPLE 25

Process Stabilization of Polypropylene at 525° F. (274° C.)

The base formulation comprises unstabilized, old technology polypropylene (PROFAX 6501, Himont) containing 0.075% by weight of calcium stearate. The test additives are incorporated into the polyproylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion | |
|---|---|---|---|
| | | 1 | 5 |
| None | — | 10.3 | 44.3 |
| AO A | 0.075 | 4.4 | 10.7 |
| Compound of Example 1 | 0.075 | 2.8 | 4.0 |

-continued

| Additive* | Concentration (% by weight) | Melt Flow after Extrusion 1 | 5 |
|---|---|---|---|
| Compound of Example 2 | 0.075 | 2.7 | 3.9 |
| Compound of Example 3 | 0.075 | 3.1 | 4.4 |
| Compound of Example 4 | 0.075 | 2.9 | 4.7 |
| Compound of Example 5 | 0.075 | 2.8 | 5.9 |
| Compound of Example 6 | 0.075 | 2.9 | 6.4 |
| Compound of Example 12 | 0.075 | 3.0 | 4.5 |

*AO A is neopentanetetrayl tetrakis(3,5-di-tert-butyl-4-hydroxyhydrocinnamate).

These results show that the substituted 3,7,9-trioxa-1-aza-2,8-diphosphaspiro[4.5]decanes provide improved melt flow stabilization to polypropylene compared to the phenolic antioxidant.

EXAMPLE 26

Color Stabilization of Polypropylene

This example illustrates the color stabilizing effectiveness of the instant compounds in combination with a phenolic antioxidant in polypropylene.

Using the procedure described in Example 25, polypropylene containing a phenolic antioxidant in combination with an instant compound is extruded into pellets. Using the pellets obtained after each of the first and third extrusions as described in Example 17, the pellets are compression molded into 125 mil (3.2 mm) thick plaques at 193° C. Specimen yellowness index (YI) values are determined according to ASTM method D1925. Lower YI values indicates less discoloration. The results along with melt flow values are given in the table below.

| Additive* | Concent. (% by wt) | Melt Flow Values after Extrusion | | Yellowness YI after Extrusion | |
|---|---|---|---|---|---|
| | | 1 | 3 | 1 | 3 |
| AO A | 0.075 | 4.4 | 8.0 | 9.5 | 8.8 |
| AO A plus Example 1 Compound | 0.075 0.075 | 2.7 | 3.6 | 6.9 | 8.6 |
| AO A plus Example 2 Compound | 0.075 0.075 | 3.0 | 3.4 | 7.3 | 8.6 |
| AO A plus Example 4 Compound | 0.075 0.075 | 2.7 | 3.6 | 6.4 | 8.2 |
| AO A plus Example 6 Compound | 0.075 0.075 | 2.7 | 3.9 | 7.0 | 8.4 |
| AO A plus Example 12 | 0.075 0.075 | 3.0 | 3.4 | 6.5 | 8.0 |

*AO A is neopentanetetrayl tetrakis(3,5-di-tert-butyl-4-hydroxyhydrocinnamate).

The combination of a phenolic antioxidant plus an instant compound provides excellent melt flow stabilization and better color stabilization than does the use of a phenolic antioxidant alone.

EXAMPLE 27

Following the general procedure of Example 25, the effectiveness of the instant compounds for providing melt flow stabilization to polypropylene containing a hindered amine coadditive is determined.

| Additive* | Concentration (% by weight) | Melt Flow after Extrusion 1 | 5 |
|---|---|---|---|
| HA 1 | 0.075 | 20.6 | 109 |
| HA 1 plus Example 1 Compound | 0.075 0.075 | 5.3 | 10.1 |
| HA 1 plus Example 3 Compound | 0.075 0.075 | 5.6 | 10.2 |

*HA 1 is condensation product of N,N'-bis(2,2,6,6-tetramethylpiperidin-4-yl)hexamethylene-diamine and 2,4-dichloro-6-tert-octylamino-s-triazine.

The addition of an instant compound to polypropylene containing a hindered amine compound results in much improved melt flow stabilization for the stabilized polypropylene.

EXAMPLE 28

Long Term Heat Aging Stabilization of Polypropylene

Extruded pellets (of Example 26), after the first pass, are compression molded into 125 mil (3.2 mm) plaques at 450° F. (232° C.) and then oven aged at 150° C. in a forced draft oven. The time, in days, to reach a yellowness index (YI) color of 50 units is deemed to represent failure. The results are given in the table below.

| Additive* | Concentration (% by weight) | Days to Failure |
|---|---|---|
| AO A | 0.075 | 23 |
| AO A plus Example 1 Compound | 0.075 0.075 | 43 |
| AO A plus Example 2 Compound | 0.075 0.075 | 32 |
| AO A plus Example 3 Compound | 0.075 0.075 | 33 |
| AO A plus Example 4 Compound | 0.075 0.075 | 40 |
| AO A plus Example 5 Compound | 0.075 0.075 | 40 |

*AO A is neopentanetetrayl tetrakis(3,5-di-tert-butyl-4-hydroxyhydrocinnamate).

The combination of an instant compound plus a phenolic antioxidant nearly doubles the long term heat aging stability of the stabilized polypropylene over that of the phenolic antioxidant alone.

EXAMPLE 29

Long Term Heat Aging Stability of Polypropylene

Extruded pellets (of Example 27), after the first pass, are compression molded into 40 mil (1.0 mm) plaques at 450° F. (232° C.) and then oven aged at 135° C. in a forced draft oven. The time, in days, to physical failure is determined by a 90° bend test. The results are shown in the table below.

| Additive* | Concentration (% by weight) | Days to Failure |
|---|---|---|
| HA 1 | 0.075 | 3 |
| HA 1 plus Example 1 Compound | 0.075 0.075 | 30 |
| HA 1 plus Example 3 | 0.075 0.075 | 26 |

-continued

| Additive* | Concentration (% by weight) | Days to Failure |
|---|---|---|
| Compound | | |

*HA 1 is condensation product of N,N'-bis(2,2,6,6-tetramethylpiperidin-4-yl)hexamethylene-diamine and 2,4-dichloro-6-tert-octylamino-s-triazine.

The addition of an instant compound to polypropylene stabilized with a hindered amine compound increases the long term aging stability of the stabilized polypropylene by nearly an order of magnitude.

EXAMPLE 30

Process Stabilization of Polypropylene at 525° F. (274° C.)

The base formulation comprises unstabilized polypropylene (PROFAX 6501, Himmont) containing 0.075% by weight of calcium stearate. The test additives are incorporated into the polypropylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion | |
|---|---|---|---|
| | | 1 | 5 |
| None | — | 11.1 | 91.5 |
| AO A | 0.075 | 6.3 | 20.8 |
| Compound of Example 7 | 0.075 | 7.2 | 28.6 |
| Compound of Example 10 | 0.075 | 6.5 | 68.6 |
| Compound of Example 11 | 0.075 | 5.9 | 66.4 |
| Compound of Example 13 | 0.075 | 4.2 | 28.2 |

*AO A is neopentanetetrayl tetrakis(3,5-di-tert-butyl-4-hydroxyhydrocinnamate).

These results show that the substituted 3,7,9-trioxa-1-aza-2,8-diphosphaspiro[4.5]decanes provide improved melt flow stabilization to new technology polypropylene compared to the phenolic antioxidant after the first extrusion.

EXAMPLE 31

Process Stabilization of Polypropylene at 525° F. (274° C)

Following the procedure of Example 30, polypropylene containing a phenolic antioxidant in combination with an instant compound is extruded and the melt flow rate (in grams/10 minutes) determined by ASTM method D1238 on the pellets obtained from the extruder after each of the first and fifth extrusions. The results are given in the table below.

| Additive* | Concent. (% by wt) | Melt Flow Values after Extrusion | |
|---|---|---|---|
| | | 1 | 5 |
| AO A | 0.075 | 6.3 | 20.8 |
| AO A plus Example 7 | 0.075 0.075 | 5.1 | 10.7 |

-continued

| Additive* | Concent. (% by wt) | Melt Flow Values after Extrusion | |
|---|---|---|---|
| | | 1 | 5 |
| Compound AO A plus Example 10 | 0.075 0.075 | 4.2 | 7.9 |
| Compound AO A plus Example 11 | 0.075 0.075 | 3.9 | 7.2 |
| Compound AO A plus Example 13 | 0.075 0.075 | 3.8 | 11.3 |

*AO A is neopentanetetrayl tetrakis(3,5-di-tert-butyl-4-hydroxyhydrocinnamate).

The combination of a phenolic antioxidant plus an instant compound provides excellent melt flow stabilization; better stabilization than obtained by the use of a phenolic antioxidant alone.

What is claimed is:

1. A process for the preparation of a compound which is a substituted 3,7,9-trioxa-1aza-2,8-diphosphaspiro[4.5]decane of formula I

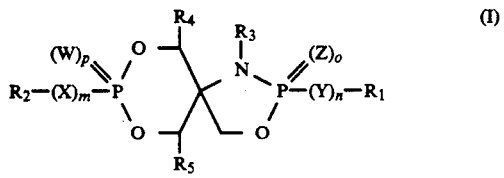

wherein
$R_1$ and $R_2$ are independently hydrogen; a linear or branched alkyl of 1 to 30 carbon atoms; said alkyl optionally terminated with —$OR_7$, —$NR_8R_9$, —$SR_{10}$, —$COOR_{11}$ or —$CONR_{12}R_{13}$, where $R_7$, $R_8$, $R_9$ and $R_{10}$ are independently alkyl of 1 to 20 carbon atoms or alkenyl of 3 to 18 carbon atoms, and $R_{11}$, $R_{12}$ and $R_{13}$ are independently hydrogen or the same meaning as $R_7$; or said alkyl interrupted by one or more —O—, —S—, —SO—, —$SO_2$—, —CO—, —COO—, —OCO—, —$CONR_{14}$, —$NR_{14}CO$— or —$NR_{15}$— where $R_{14}$ and $R_{15}$ have the same meaning as $R_{11}$; alkenyl of 3 to 30 carbon atoms; aryl of 6 to 10 carbon atoms; said aryl substituted by one to three substitutents selected from the group consisting of alkyl of 1 to 20 carbon atoms, cycloalkyl of 5 to 12 carbon atoms, phenylalkyl of 7 to 15 carbon atoms and the group —$(CH_2)_kCOOR_{20}$ where k is 0, 1 or 2 and $R_{20}$ is hydrogen, alkyl of 1 to 20 carbon atoms or cycloalkyl of 5 to 12 carbon atoms; phenylalkyl of 7 to 9 carbon atoms; bicycloalkyl of 7 to 18 carbon atoms; or tricycloalkyl of 10 to 20 carbon atoms; or $R_1$ and $R_2$ are independently a group of formula II

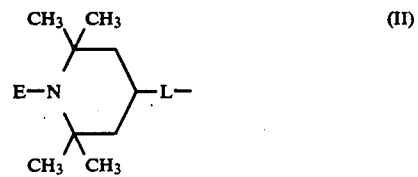

where E is hydrogen, —OH, alkyl of 1 to 18 carbon atoms, alkenyl of 3 to 18 carbon atoms, aralkyl of 7 to 15 carbon atoms, alkoxy of 1 to 18 carbon atoms or cycloalkoxy of 5 to 12 carbon atoms; and L is —O— or —NT— where T hydrogen, alkyl of 1 to 18 carbon atoms or cycloalkyl of 5 to 12 carbon atoms; or when n or m is zero, $R_1$ or $R_2$ is also independently F, Cl, Br or I;

$R_3$ is hydrogen, alkyl of 1 to 20 carbon atoms, phenylalkyl of 7 to 15 carbon atoms or aryl of 6 to 10 carbon atoms;

$R_4$, $R_5$ and $R_6$ are independently hydrogen, alkyl of 1 to 4 carbon atoms or aryl of 6 to 10 carbon atoms;

X and Y are indepedently —O—, —S— or —$NR_{16}$— where $R_{16}$ is hydrogen, alkyl of 1 to 20 carbon atoms, cycloalkyl of 5 to 12 carbon atoms, alkenyl of 3 to 18 carbon atoms, aryl of 6 to 10 carbon atoms, said aryl substituted by one or two alkyl of 1 to 4 carbon atoms; or phenylalkyl of 7 to 15 carbon atoms;

W and Z are independently O or S; and n, m, o and p are independently zero or 1, which comprises transesterifying a compound of formula IV

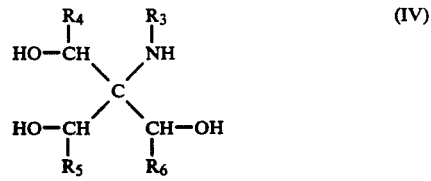

with an essentially stoichiometric amount of a trialkyl or triaryl phosphite of the formula $(R_1O)_3P$ or $(R_2O)_3P$ or mixture thereof in the presence of an alkali metal amide, alkoxide or phenoxide catalyst, wherein $R_1$ to $R_6$ are as defined above.

2. A process according to claim 1 wherein the process is carried out in the presence of an inert solvent.

* * * * *